(12) United States Patent
Ogata et al.

(10) Patent No.: US 6,387,882 B1
(45) Date of Patent: May 14, 2002

(54) VITAMIN E DERIVATIVES

(75) Inventors: Kazumi Ogata, Osaka; Hidetoshi Nakao, Hyogo; Kazuhiko Ito, Hyogo; Takahiro Sakaue, Hyogo; Masahito Iemura, Kyoto; Yutaka Inoue, Osaka, all of (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/581,588

(22) PCT Filed: Dec. 18, 1998

(86) PCT No.: PCT/JP98/05765

§ 371 Date: Jun. 15, 2000

§ 102(e) Date: Jun. 15, 2000

(87) PCT Pub. No.: WO99/33818

PCT Pub. Date: Jul. 8, 1999

(30) Foreign Application Priority Data

Dec. 24, 1997 (JP) .............................. 9-354979
Jun. 26, 1998 (JP) ............................. 10-180831

(51) Int. Cl.[7] .................. A61K 7/00; A61K 31/355; A61K 31/40; A61K 38/05; A61K 38/06

(52) U.S. Cl. .................. 514/18; 514/19; 514/458; 530/331; 530/332; 530/345; 549/410

(58) Field of Search ............. 424/401; 514/18, 514/19, 458; 530/331, 332, 345; 549/410

(56) References Cited

U.S. PATENT DOCUMENTS 3,657,279 A   4/1972  Higashi et al. ............. 549/410
4,564,686 A   1/1986  Ogata ........................ 549/220
4,665,204 A * 5/1987  Wirth ......................... 549/410
4,914,197 A   4/1990  Yamamoto et al. ......... 536/117
5,606,080 A   2/1997  Ogata et al. ................ 549/408
5,811,083 A * 9/1998  Pelle et al. ................... 424/59

FOREIGN PATENT DOCUMENTS

JP   02-44478   10/1990
JP   05-23274    4/1993
JP   08-34779    2/1996

* cited by examiner

*Primary Examiner*—Jeffrey E. Russel
(74) *Attorney, Agent, or Firm*—Merchant & Gould PC

(57) ABSTRACT

The present invention provides novel vitamin E derivatives represented by the following formula (I) wherein: $R_1$ and $R_2$ are the same or different and each denotes hydrogen or methyl, $R_3$ denotes an S-linked SH compound (glutathione, γ-glutamylcysteine, cysteine, penicillamine, an ester thereof or cysteamine), and $R_4$ denotes hydroxyl, a N-substituted amino acid (glycine, β-alanine, γ-aminobutyric acid, 5-aminovaleric acid, ε-aminocaproic acid, anthranilic acid, tranexamic acid, proline, an ester thereof, aminoethylsulfonic acid, aminoethylsulfinic acid) or serotonin, or a pharmacologically acceptable salt thereof, which are useful as hepatopathy suppressing agents, anticataract agents, cerebral metabolism improving agents, antioxidants and cosmetic components.

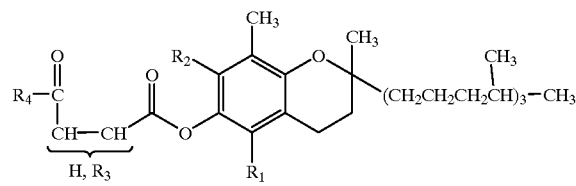

23 Claims, 8 Drawing Sheets

VITAMIN E DERIVATIVES

TECHNICAL FIELD

The present invention relates to novel water soluble vitamin E derivatives, method for their production, and their use. In further detail, the present invention relates to novel vitamin E derivatives which are made up of vitamin E maleate (or fumarate) and an S-linked SH compound attached to it, as well as such novel vitamin E derivatives which further include an amino acid or its ester or an amine linked via an acid amide bond, a method for their production, and to hepatopathy suppressing, anticataract, cerebral metabolism improving and antioxidant pharmaceutical compositions and cosmetic compositions containing one of them.

BACKGROUND ART

Vitamin E ($\alpha$, $\beta$, $\gamma$, $\delta$-tocopherol) has an antioxidant activity and it has been suggested recently that the compound is effective against cataract. While vitamin E by itself is insoluble in water, there are known water-soluble vitamin E derivatives created by the present inventors such as a phosphodiester compound consisting of vitamin E and vitamin C (ascorbic acid) (Japanese Patent Publication No. H02-44478, Japanese Patent Publication No. H05-23274), as well as a vitamin E glycidyl glutathione compound (Japanese Laid-open Patent Application No. H08-34779).

The present inventors, as a result of further investigations for a novel water-soluble vitamin E derivative, have succeeded in synthetically producing the water-soluble vitamin E derivatives of the present invention. The present invention is accomplished based on these and still further investigations.

DISCLOSURE OF INVENTION

The present invention relates to:
(1) a vitamin E derivative represented by the following formula (I) wherein: $R_1$ and $R_2$ are the same or different and each denotes hydrogen or methyl, $R_3$ denotes one of the S-linked SH compounds as defined hereinbelow or an ester thereof (except cysteamine), and $R_4$ denotes hydroxyl, one of the N-substituted amino acids defined hereinbelow or an ester thereof (except aminoethylsulfonic acid and aminoethylsulfinic acid) or the amine defined hereinbelow, or a pharmacologically acceptable salt thereof (hereinafter referred to as "the present compound"),

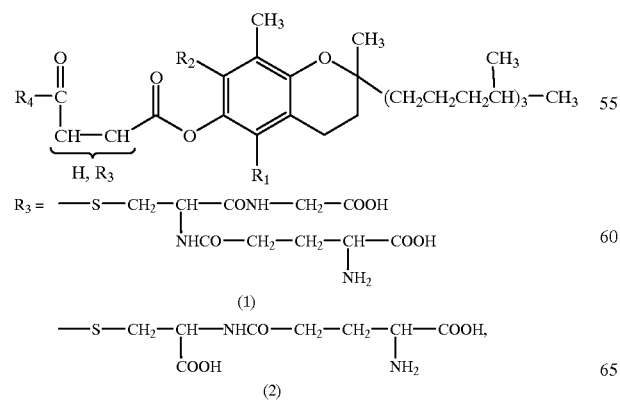

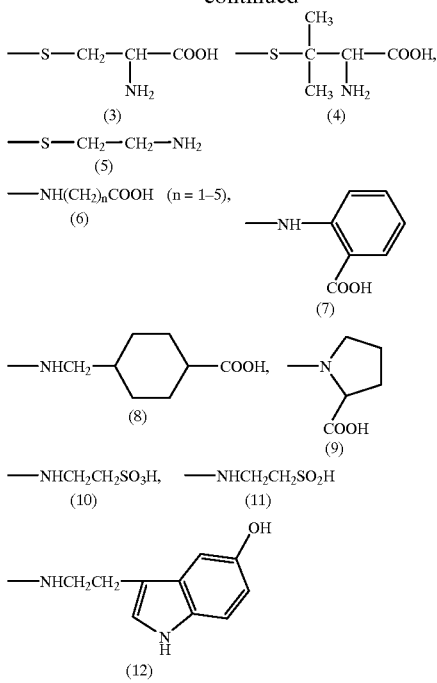

(2) a mono-tocopheryl maleate (or fumarate) represented by the following formula (IV) wherein: $R_1$ and $R_2$ are the same or different and each denotes hydrogen or methyl,

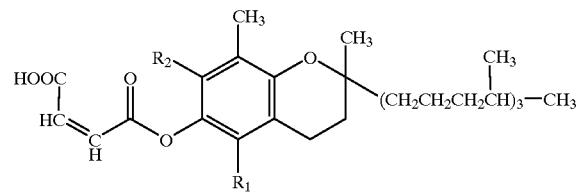

(3) a method for preparation of a vitamin E derivative as defined in (2) above or a pharmacologically acceptable salt thereof which comprises reacting vitamin E with maleic anhydride,
(4) a method for preparation of a vitamin E derivative as defined in (1) above or a pharmacologically acceptable salt thereof which comprises: reacting vitamin E with maleic anhydride to produce mono-tocopheryl maleate (or fumarate) and then subjecting the thus produced mono-tocopheryl maleate (or fumarate) to an addition reaction with a compound selected from the group of SH compounds consisting of glutathione, $\gamma$-glutamylcysteine, cysteine, penicillamine, esters thereof, and cysteamine,
(5) a method for preparation of a vitamin E derivative as defined in (1) above or a pharmacologically acceptable salt thereof which comprises: reacting vitamin E with maleic anhydride to produce mono-tocopheryl maleate (or fumarate) and then subjecting the thus produced mono-tocopheryl maleate (or fumarate) to a condensation reaction with a compound selected from the group of amino acids consisting of glycine, $\beta$-alanine, $\gamma$-aminobutyric acid, 5-aminovaleric acid, $\epsilon$-aminocaproic acid, anthranilic acid, tranexamic acid, proline, esters thereof, aminoethylsulfonic acid and aminoethylsulfinic acid or with serotonin by mixed acid anhydride method to produce a corresponding acid amide of the monotocopheryl maleate (or fumarate), and then subjecting the product to an addition reaction with a compound selected from the group of SH compounds consisting of glutathione, γ-glutamylcysteine, cysteine, penicillamine, esters thereof, and cysteamine, (6) a hepatopathy suppressing pharmaceutical composition comprising the compound as defined in (1) above or a pharmacologically acceptable salt thereof, (7) an anticataract pharmaceutical composition comprising the compound as defined in (1) above or a pharmacologically acceptable salt thereof, (8) a cerebral metabolism improving pharmaceutical composition comprising the compound as defined in (1) above or a pharmacologically acceptable salt thereof, (9) an antioxidant pharmaceutical composition comprising the compound as defined in (1) above or a pharmacologically acceptable salt thereof, and

(10) a cosmetic composition comprising the compound as defined in (1) above or a pharmacologically acceptable salt thereof.

DETAILED DESCRIPTION OF THE INVENTION

Figure 1:
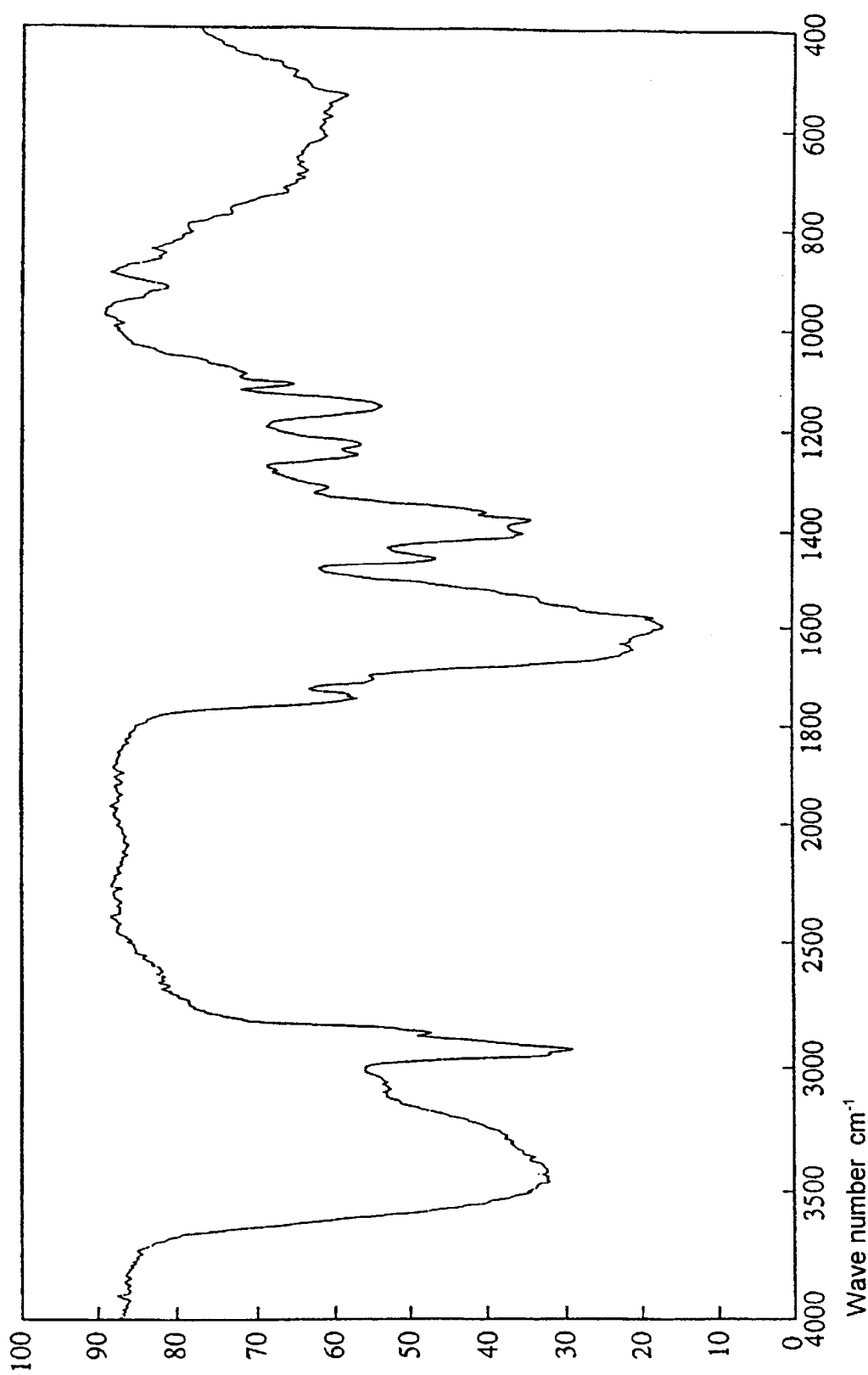
FIG. 1 shows an infrared spectrum (IR) of the compound synthesized in Example 1.

The present compound, as represented by formula (I), is of a chemical structure made up of vitamin E (α, β, γ, δ-tocopheryl) maleate (or fumarate) with an S-linked SH compound attached to it, or of a chemical structure further including an amino acid or amine attached to it.

In formula (I), examples of SH compounds for $R_3$ include (1) glutathione, (2) γ-glutamylcysteine, (3) cysteine, (4) penicillamine, their esters, and (5) cysteamine.

In formula (I), examples of N-substituted amino acids for $R_4$ include (6) glycine (n=1 in the formula), β-alanine (n=2 in the formula), γ-aminobutyric acid (n=3 in the formula), 5-aminovaleric acid (n=4 in the formula), ε-aminocaproic acid (n=5 in the formula), (7) anthranilic acid, (8) tranexamic acid, (9) proline, their esters, (10) aminoethylsulfonic acid, and (11) aminoethylsulfinic acid.

In formula (I), examples of amines for $R_4$ include (12) serotonin.

Specific examples of the present compound include the following compounds and their pharmacologically acceptable salts.

(1) S-[2-carboxy-1-(α-tocopheryl-6-yl-oxycarbonyl) ethyl]glutathione (2) S-[2-(N-carbonylaminoethylsulfonic acid)-1-(α-tocopheryl-6-yl-oxycarbonyl)ethyl]glutathione (3) S-[2-(N-carbonylanthranilic acid)-1-(α-tocopheryl-6-yl-oxycarbonyl)ethyl]glutathione (4) S-[2-(N-carbonyl-γ-aminobutyric acid)-1-(α-tocopheryl-6-yl-oxycarbonyl)ethyl]glutathione (5) S-[2-(N-carbonylaminoethylsulfonic acid)-1-(α-tocopheryl-6-yl-oxycarbonyl)ethyl]cysteine (6) S-[2-(N-carbonyl-3-β-aminoethyl-5-hydroxyindol)-1-(α-tocopheryl-6-yl-oxycarbonyl)ethyl]glutathione (7) S-[2-(N-carbonyl-6-amino-n-caproic acid)-1-(α-tocopheryl-6-yl-oxycarbonyl)ethyl]glutathione (8) S-[2-(N-carbonyl-trans-4-aminomethylcyclohexanecarboxylic acid)-1-(α-tocopheryl-6-yl-oxycarbonyl)ethyl]glutathione (9) S-[2-(N-carbonylaminoethylsulfonic acid)-1-(α-tocopheryl-6-yl-oxycarbonyl)ethyl]γ-glutamylcysteine

(10) S-[2-(N-carbonylaminoethylsulfonic acid)-1-(α-tocopheryl-6-yl-oxycarbonyl)ethyl]penicillamine

(11) S-[2-(N-carbonylaminoethylsulfonic acid)-1-(α-tocopheryl-6-yl-oxycarbonyl)ethyl]cysteamine

(12) S-[2-(N-carbonylglycineethyl)-1-(α-tocopheryl-6-yl-oxycarbonyl)ethyl]glutathione

(13) S-[2-(N-carbonylaminoethylsulfonic acid)-1-(α-tocopheryl-6-yl-oxycarbonyl)ethyl]glutathione isopropyl ester

(14) S-[2-(N-carbonylaminoethylsulfinic acid)-1-(α-tocopheryl-6-yl-oxycarbonyl)ethyl]glutathione

(15) S-[2-(N-carboxypropyl)-1-(α-tocopheryl-6-yl-oxycarbonyl)ethyl]glutathione.

The present compound can be used for the purposes of the present invention either in its free form or in the form of its pharmacologically acceptable salt. Examples of its pharmacologically acceptable salt include alkaline metal salts such as sodium salt and potassium salt, and alkaline earth metal salts such as calcium salt and magnesium salt, as well as organic amine salts such as ethanolamine salt and lysine salt. Any other salts may be used insofar as they are pharmacologically acceptable.

As vitamin E, a component of the present compound, any of α, β, γ and δ-tocopherol may be employed. As aforementioned, vitamin E is an antioxidant, and it has been suggested in recent years that vitamin E is effective against cataract.

As an SH compound, another component of the present compound, (1) glutathione, (2) γ-glutamylcysteine, (3) cysteine, (4) penicillamine, their esters, and (5) cysteamine may be used, as aforementioned. Among them, glutathione, γ-glutamylcysteine and cysteine are respectively known to be effective as anticataract and hepatopathy suppressing agents. Penicillamine is used in the therapy of rheumatoid arthritis, for detoxification in metal poisoning, and in the therapy of Wilson's disease. Cysteamine still is one of the most effective radiation protector compounds.

Example of the esters of glutathione, γ-glutamylcysteine, cysteine, and penicillamine include esters with alkyl of 2 to 6 carbon atoms. Specifically, they include methyl ester, ethyl ester, n-propyl ester, isopropyl ester, cyclopropyl, n-butyl ester, tert-butyl ester, sec-butyl ester, n-pentyl ester, 1-ethylpropyl ester, and isopentyl ester.

As an amino acid, a third component of the present compound, (6) glycine (n=1 in the formula), β-alanine (n=2 in the formula), γ-aminobutyric acid (n=3 in the formula), 5-aminovaleric acid (n=4 in the formula), ε-aminocaproic acid (n=5 in the formula), (7) anthranilic acid, (8) tranexamic acid, their esters, aminoethylsulfonic acid, or aminoethylsulfinic acid is used as aforementioned.

Among the above amino acids, glycine is used as an antidote, β-alanine is a component of pantothenic acid, and γ-aminobutyric acid is known to be a cerebral neurotransmitter. 5-aminovaleric acid is a GABA (γ-aminobutyric acid) agonist, and ε-aminocaproic acid is known to be an antiplasmin agent. Anthranilic acid (also named o-aminobenzoic acid) has been found to have vitamin L activity in mammals, tranexamic acid is known as an anti-plasmin agent, and proline is an non-essential amino acid. Aminoethylsulfonic acid (also named taurine), which occurs at higher levels in the liver and the muscle, has a property characteristic of an amphoteric electrolyte as amino acid, and aminoethylsulfinic acid (also named hypotaurine), which occurs in normal rat urine, rat brain as well as in molluscs, is an intermediate product of taurine production through oxidation of cysteine in animals and is produced from its precursor, cysteinesulfinic acid, through decarboxylation by cysteinesulfinic acid decarboxylase, which is a pyridoxal enzyme.

Example of the esters of the amino acids (except aminoethylsulfonic acid and aminoethylsulfinic acid) include esters with alkyl of 2 to 6 carbon atoms. Specifically, they include methyl ester, ethyl ester, n-propyl ester, isopropyl ester, cyclopropyl, n-butyl ester, tert-butyl ester, sec-butyl ester, n-pentyl ester, 1-ethylpropyl ester, and isopentyl ester.

As an amine, a third component of the present compound, serotonin is employed, which is known to be a cerebral neurotransmitter.

The present compound can be synthesized through the following route of synthesis, for example, or analogously to it.

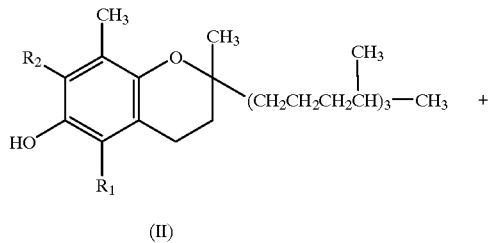

(II)

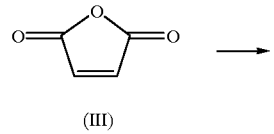

(III)

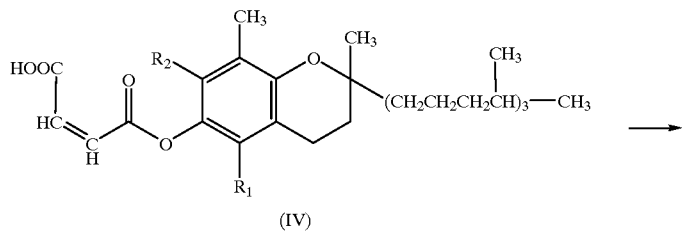

(IV)

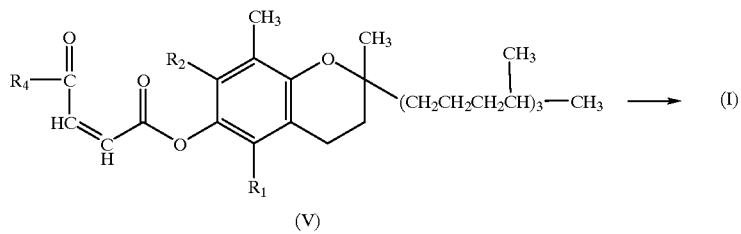

(V)

(In the reaction scheme, $R_1$, $R_2$ and $R_4$ are as defined hereinbefore.)

Specifically, the procedure is as follows. First, vitamin E (II) is reacted with maleic anhydride (III) in the presence of an alkaline carbonate (sodium carbonate, potassium carbon ate or the like) or an alkaline acetate (sodium acetate, potassium acetate or the like) in a nonpolar solvent such as acetone, acetonitrile or tetrahydrofuran (THF) for about 1 to 3 hours while heating to give mono-tocopheryl maleate (or fumarate) (IV) (which is a novel compound not found in publications so far). The compound (IV) thus produced may further be subjected to a condensation reaction with an amino acid (glycine, β-alanine, γ-aminobutyric acid, 5-aminovaleric acid, ε-aminocaproic acid, anthranilic acid, tranexamic acid, proline, one of their esters, aminoethylsulfonic acid, or aminoethylsulfinic acid) or an amine (serotonin) in a solvent such as chloroform or tetrahydrofuran in the presence of an organic amine (pyridine, triethylamine or the like) according to the mixed anhydride method using ethyl chloroformate or the like to give a corresponding acid amide (V) of mono-tocopheryl maleate (or fumarate) (IV). The compound (IV) or (V) then is subjected to an addition reaction with an SH compound (glutathione, γ-glutamylcysteine, cysteine, penicillamine, an ester thereof, or cysteamine), a component of the present compound, at room temperature for about 3 to 6 hours and then about 1 to 3 hours while warming to give the present compound (I). A reaction solvent for this may be water or a solvent miscible with water, e.g., alcohol, acetonitrile or dioxane, which preferably is used as a mixture with water.

The present compound (I) thus obtained may be converted to a pharmacologically acceptable salt by a known method.

The present compound (I) thus obtained is a novel compound not found in publications so far, and can be used as a hepatopathy suppressing agent, anticataract agent, cerebral metabolism improving agent, and an antioxidant as well as a component of cosmetic compositions as the present compound, in the body, is expected to be cleaved at the S-link within it into vitamin E and a corresponding SH compound, or cleaved at the acid amide bond within it into a corresponding amino acid or amine.

The hepatopathy suppressing pharmaceutical composition of the present invention is useful to prophylaxis and treatment of acute or chronic hepatitis, for it effectively suppresses the development of either acute or chronic hepatopathy, while suppressing elevation of GOP and GPT levels. It can also be used advantageously against hepatopathy induced by a drug such as acetaminophen.

Examples of diseases to which the cerebral metabolism improving pharmaceutical composition of the present invention is addressed, in particular, are cerebrovascular diseases such as cerebral infarction and cerebral apoplexy.

Unlike vitamin E, which is insoluble in water, as the present compound is provided as non-hygroscopic, stable crystals soluble in water, it is useful in the preparation of aqueous compositions such as injections and eye drops.

When it is used in a hepatopathy suppressing, anticataract or cerebral metabolism improving pharmaceutical composition, one of the species of the present compound, or two or more of them in combination, may be included in accordance with the purpose and needs.

The present compound may be used orally or parenterally in a hepatopathy suppressing, anticataract or cerebral metabolism improving pharmaceutical composition. Any of pharmaceutical composition forms including solid compositions such as tablets, granules, powders and capsules or liquid compositions such as injections or eye drops may be prepared by known methods. Such pharmaceutical compositions may, as needed, contain conventionally employed additives such as excipients, binders, thickeners, dispersing agents, resorption enhancers, buffering agents, surfactants, solubilizers, preservatives, emulsifiers, isotonizers, stabilizers, pH adjusting agents and the like.

When used in hepatopathy suppressing, anticataract or cerebral metabolism improving pharmaceutical compositions, the dose of the present compound preferably is: e.g., about 1 mg to about 30 mg once a day for adults for injections, and about 1 mg to about 100 mg at a time, which is repeated several times a day for adults for oral composition, though the dose may vary m accordance with the specific compound used, the body weight and age of the patient, the disease and its condition to be dealt with and the route of dosage. For eye drops, preferably one with a concentration of about 0.01 to 5 (w/v)% is applied a few drops at a time, which is repeated several times a day for adults.

A pharmaceutical composition containing the present compound may further contain other pharmacologically active ingredients such as hepatopathy suppressing, anticataract, cerebral metabolism improving agents or other types of pharmacologically active ingredients insofar as they do not contradict the purpose of the present invention.

With respect to its use as a cosmetic material, the present compound may be added to creams, lotions or toilet waters and the like in order for absorption of ultraviolet light or skin-beautifying effect or for stabilization (anti-oxidation) of other materials contained in cosmetic compositions. Cosmetic compositions containing the present compound may contain other materials conventionally employed in cosmetic compositions.

When used as a cosmetic material, the present compound is usually contained at a concentration of about 0.001 to 5 (w/w)%, preferably about 0.005 to 2 (w/w)%, though it may vary in accordance with the specific compound used, the type of the cosmetic composition to which the compound is to be added and the purpose of the addition of the compound.

BEST MODE FOR CARRYING OUT THE INVENTION

The present invention will be described in further detail below with reference to examples and composition examples. The scope of the present invention, however, is not limited to those examples.

EXAMPLE 1

S-[2-Carboxy-1-(α-tocopheryl-6-yl-oxycarbonyl) Ethyl]glutathione 80 ml of acetone was added to 4.3 g (0.01 mol) of dl-α-tocopherol, 2.0 g (0.02 mol) of maleic anhydride and 2.1 g (0.02 mol) of sodium carbonate, refluxed for 1 hour while heating, inorganic salts were filtered out, and the solvent was evaporated. To the residual oil was added 60 ml of water, acidified with hydrochloric acid, and extracted with ethyl acetate. After washing the extract with water, evaporation of ethyl acetate gave about 5 g of maleic acid mono-α-tocopherol ester as residual oil. 0.6 g of sodium hydroxide and 3.4 g (0.011 mol) of glutathione were added to 100 ml of 70% methanol and dissolved. To this solution was added the above maleic acid mono-α-tocopherol ester dissolved in 30 ml of methanol, and stirred for 3 hours at 40° C. After cooling, precipitated semisolid oil was collected, washed with 80% aqueous methanol 2 to 3 times, and crystallized by addition of methanol. 4.0 g of crystals were obtained through collection by filtration and washing with acetone. Recrystallization of the crystals from water-ethanol gave 2.8 g of monosodium salt of the aimed compound. Its IR spectrum is shown in FIG. 1.

Elemental analyses: for $C_{43}H_{68}N_3O_{11}SNa \cdot 1.5 H_2O$; Calculated (%): C, 58.35; H, 8.09; N, 4.75; Found (%): C, 58.09; H, 8.15; N, 5.00.

Figure 2:
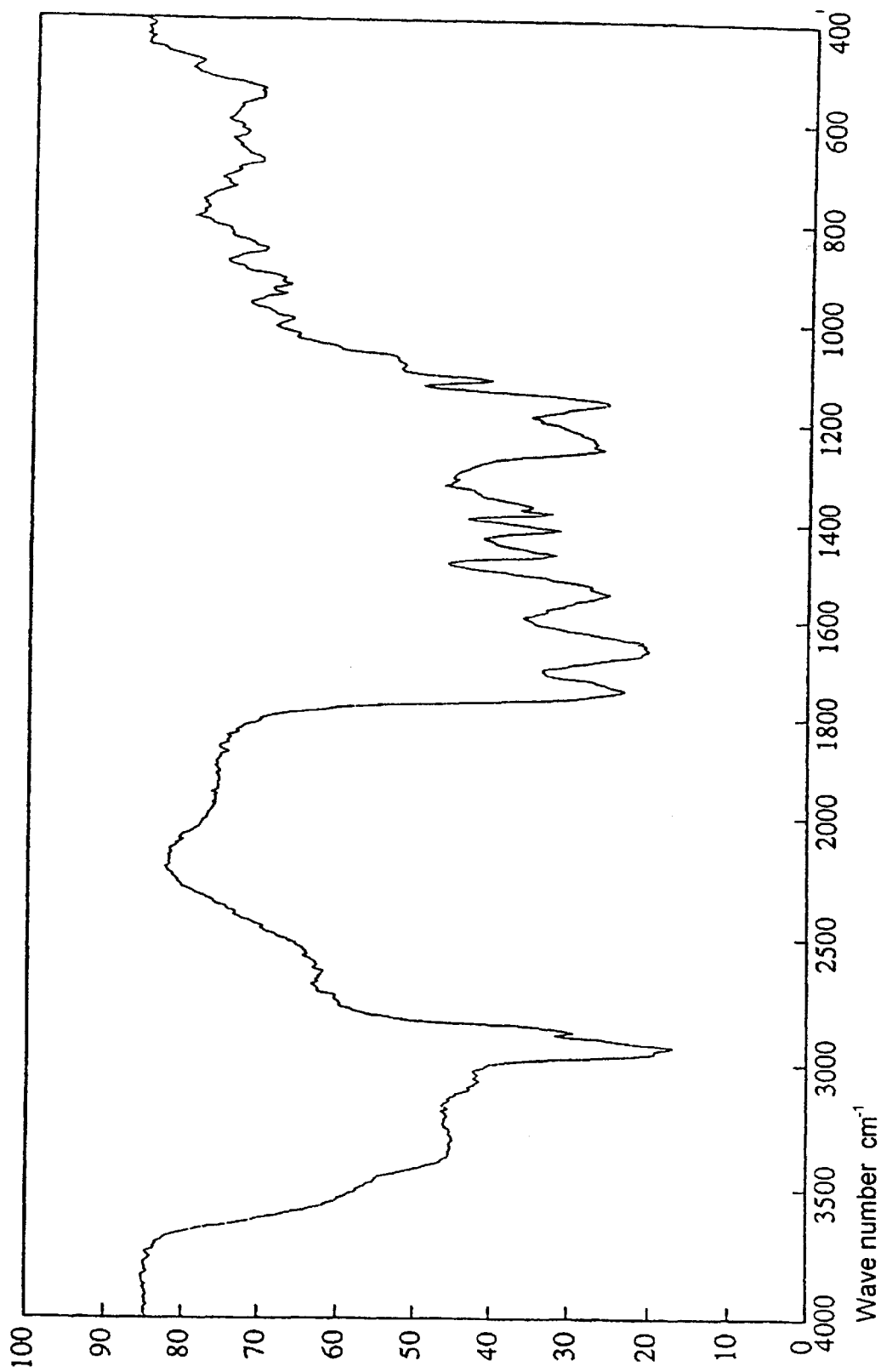
FIG. 2 shows an infrared spectrum (IR) of the compound synthesized by the Alternative Method in Example 1.

Alternative Method: S-[2-Carboxy-1-(α-tocopheryl-6-yl-oxycarbonyl)ethyl]glutathione 80 ml of acetone was added to 4.3 g of dl-α-tocopherol, 3.0 g of maleic anhydride and 1.5 g of sodium acetate, refluxed for 3 hours while heating, and the solvent was evaporated. To the residual oil was added 60 ml of water, acidified with hydrochloric acid, and extracted with diisopropyl ether. After washing with water, evaporation of diisopropyl ether gave 5.1 g of maleic acid mono-α-tocopherol ester as residual oil (which crystallized after having been let stand) (which would give 3.8 g of while crystals, m.p. 70–72° C., when recrystallized from n-hexane). 0.6 g of sodium hydroxide was dissolved in 80 ml of methanol. To this solution were added 3.4 g of glutathione and the above maleic acid mono-α-tocopherol ester dissolved in 30 ml of ethanol, and stirred for 3 hours at 50° C. After cooling, precipitated white crystals were collected by filtration, and washed with acetone. 100 ml of water then was added to the crystals to form a paste, and its pH was adjusted to 3 by addition of hydrochloric acid. White crystals precipitated were collected by filtration, washed with water, dried, and recrystallized from tetrahydrofuran/ethanol to give 3.5 g of the free acid, m.p. 200–202° C. (decomp.). Its IR spectrum is shown in FIG. 2. TLC: silica gel Rf=0.35 (n-butanol:acetic acid:water =4:1:1).

Elemental analyses: for $C_{43}H_{69}N_3O_{11}S \cdot H_2O$; Calculated (%): C, 60.47; H, 8.37; N, 4.92; Found (%): C, 60.53; H, 8.57; N, 5.14.

Then, 3.5 g of the above free acid was dissolved in 60 ml of tetrahydrofuran, pH of the solution adjusted to 6.5 by gradual addition of sodium hydroxide/methanol, and the solvent evaporated. To this was added methanol and white crystals precipitated were collected by filtration. Recrystallization from water-methanol gave 3.0 g of disodium salt of the aimed compound, m.p., 230–232° C. (decomp.).

Elemental analyses: for $C_{43}H_{67}N_3O_{11}SNa_2 \cdot 1.5 H_2O$; Calculated (%): C, 56.94; H, 7.77; N, 4.63; Found (%): C, 56.62; H, 7.98; N, 4.75.

EXAMPLE 2

S-[2-(N-Carbonylaminoethylsulfonic acid)-1-(α-tocopheryl-6-yl-oxycarbonyl)ethyl]glutathione 5.3 g of the intermediate compound, maleic acid mono-α-tocopherol ester obtained in Example 1 was dissolved in 30 ml of chloroform, and to this solution was added 1.2 g of triethylamine. After cooling to −5° C., 1.3 g of ethyl chloroformate was added to the solution dropwise, and, 15 min later, 1.6 g of aminoethylsulfonic acid and 0.5 g of sodium hydroxide dissolved in 50 ml of methanol was added at a stroke to the solution, stirred for 30 min, and for further 1 hour after the mixture was brought back to room temperature. The solvent was evaporated and acetone added. White crystals precipitated were collected by filtration to give 4.0-g product. The mother liquid was adjusted to pH 8 by addition of sodium hydroxide/methanol, and crystals thus precipitated were collected by filtration to give 1.6-g product. These and previous crystals were combined and recrystallized from methanol/ethanol to give 4.5 g of the sodium salt of 2-(N-carbonylamino-ethylsulfonic acid)-1-(α-tocopheryl-6-yl-oxycarbonyl)ethylene, m.p. 185–187° C.

Figure 3:
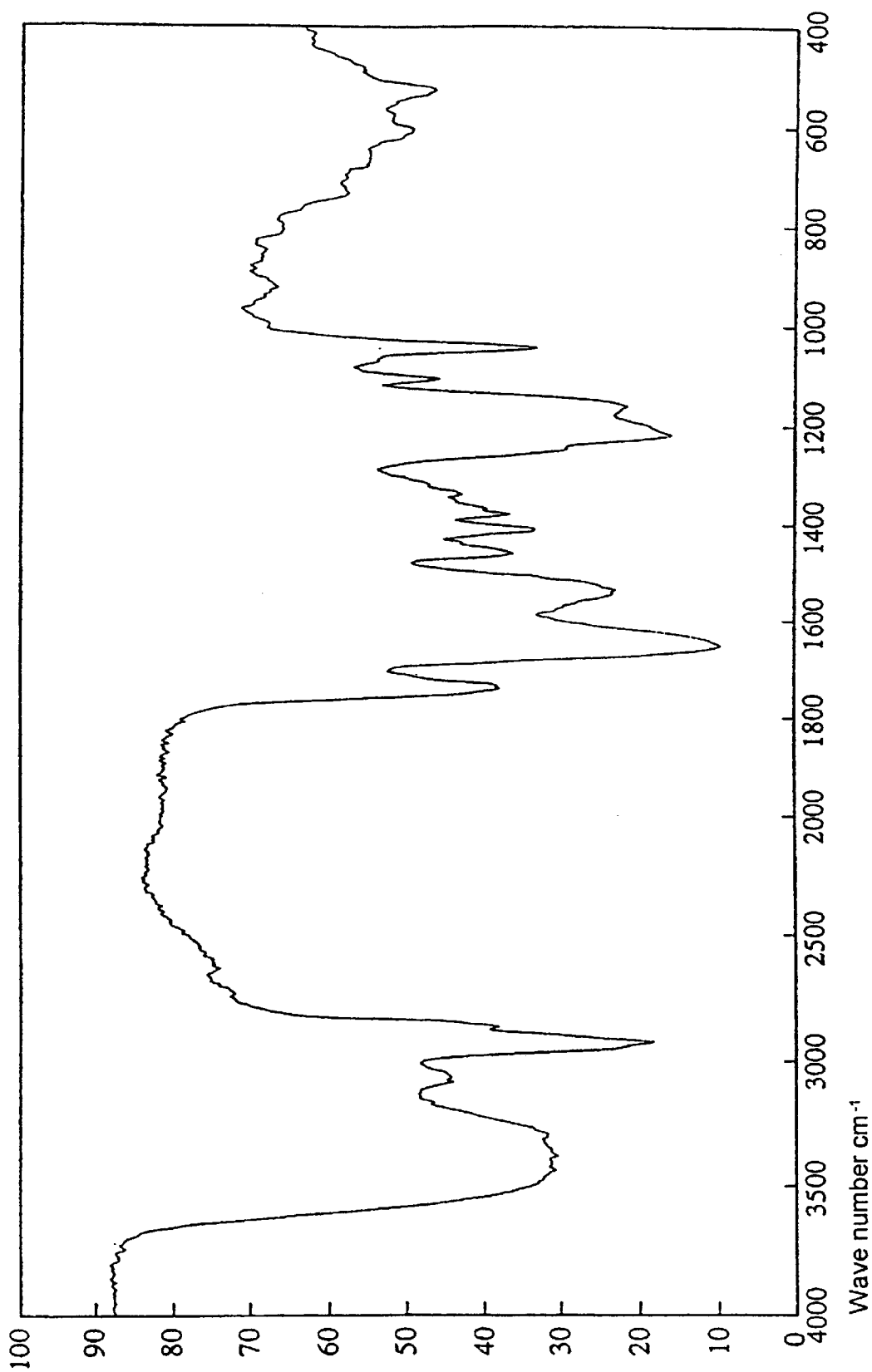
FIG. 3 shows the infrared spectrum (IR) of the compound synthesized in Example 2.

To 60 ml of 90 (V/V)% methanol solution were added 0.45 g of sodium hydroxide and 3.3 g of glutathione to dissolve. To this solution was added 4.5 g of the above compound dissolved in 50 ml of methanol and stirred for 3 hours at 50° C. After cooling, white crystals precipitated were collected by filtration, and washed with methanol to give 6.0-g product. This was dissolved in 200 ml of water and to the solution was added 2.5 g copper acetate dissolved in 50 ml of water plus 2 ml of acetic acid. Precipitated copper salt was collected by filtration, washed with water, acetone and then methanol to give 5.3-g product. The product was suspended in 100 ml of a tetrahydrofuran/methanol (3:5) mixture solution and hydrogen sulfide was passed in. After removing copper sulfide by filtration, the filtrate was adjusted to pH5 by addition of sodium hydroxide/methanol. White crystals precipitated were collected by filtration, washed with methanol, and dried to give 3.9 g of sodium salt of the aimed compound, m.p. 235–237° C. (decomp.). Its IR spectrum is shown in FIG. 3. TLC: silica gel Rf=0.18 (n-butanol:acetic acid:water 4:1:1).

Elemental analyses: for $C_{45}H_{73}N_4O_{13}S_2Na \cdot 4 H_2O$; Calculated (%): C, 52.11; H, 7.87; N, 5.40; Found (%): C, 52.46; H, 7.67; N, 5.62.

EXAMPLE 3

S-[2-(N-Carbonylanthranihc acid)-1-(α-tocopheryl-6-yl-oxycarbonyl)ethyl]glutathione 5.3 g of the intermediate compound, maleic acid mono-α-tocopherol ester, obtained in Example 1 was dissolved in 30 ml of chloroform and reacted as in Example 1 with 1.5 g of anthranilic acid plus 3 ml of pyridine dissolved in 40 ml of tetrahydrofuran according to the mixed anhydride method using 1.2 g of triethylamine and 1.3 g of ethyl chloroformate. After evaporation of the solvent and acidification with hydrochloric acid, extraction with ethyl acetate, washing with water, evaporation of ethyl acetate gave 7.5 g of residual oil.

Separately, 0.8 g of sodium hydroxide was dissolved in 70 ml of methanol. To this solution was added 3.3 g of glutathione and 7.5 g of the above oil dissolved in 20 ml of methanol, and stirred for 3 hours at 50° C. After cooling, white crystals precipitated were collected by filtration. 50 ml of water was added to the crystals to form a gel. To this was added 3 ml of acetic acid and white crystals precipitated were collected by filtration, dissolved in ethyl acetate/ethanol mixed solution. After adjusting its pH to 6.5 by addition of sodium hydroxide/methanol, white crystals precipitated were collected by filtration, recrystallized from tetrahydrofuran/ethanol to give 3.7 g of sodium salt of the aimed compound, m.p. 202–204° C. TLC: silica gel Rf=0.46 (n-butanol:acetic acid:water=4:1:1).

Elemental analyses: for $C_{50}H_{72}N_4O_{12}SNa_2 \cdot 3H_2O$; Calculated (%): C, 57.02; H, 7.46; N, 5.32; Found (%): C, 56.93; H, 7.74; N, 5.19.

EXAMPLE 4

Figure 4:
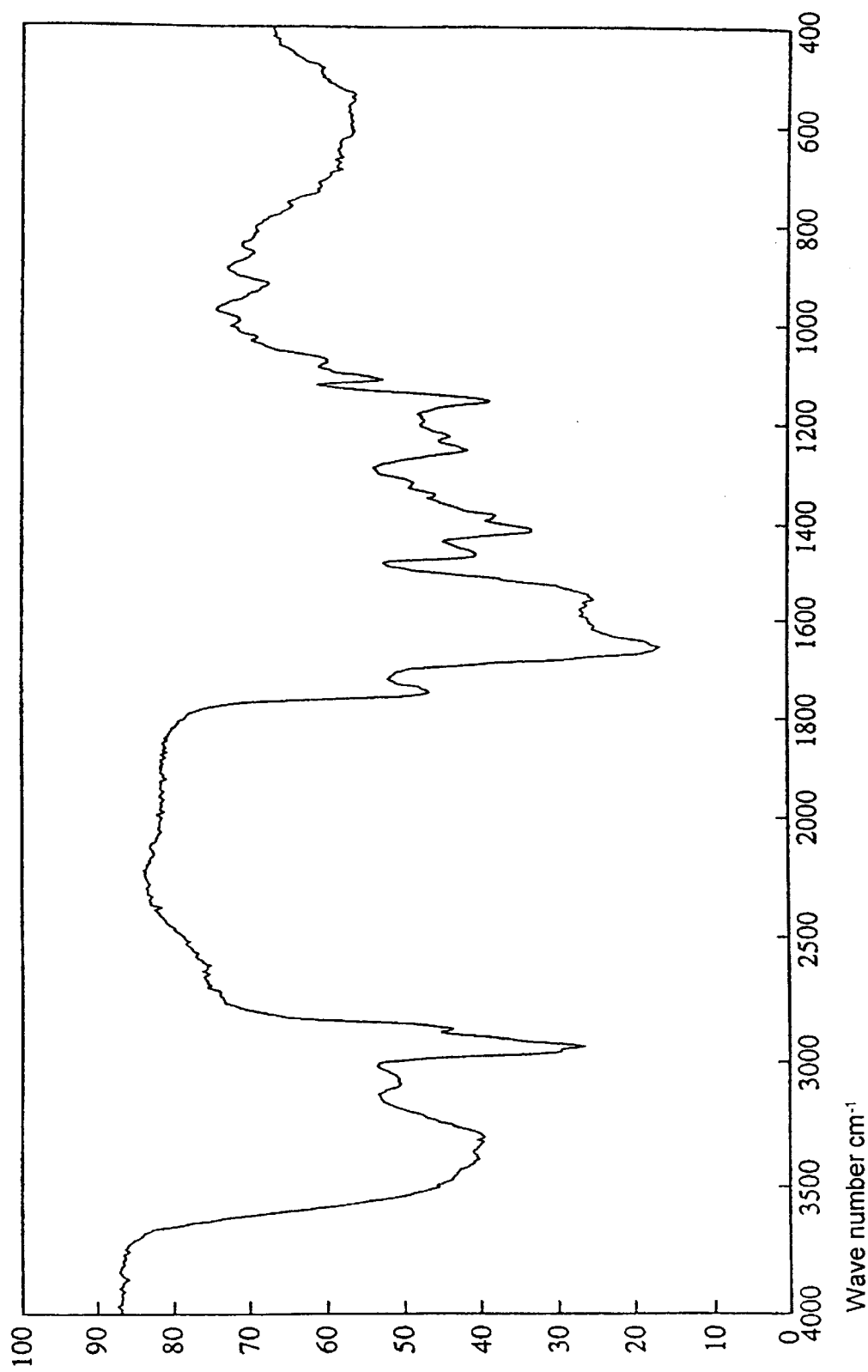
FIG. 4 shows an infrared spectrum (IR) of the compound synthesized in Example 4.

S-[2-(N-Carbonyl-γ-aminobutyric acid)-1-(α-tocopheryl-6-yl-oxycarbonyl)ethyl]glutathione 5.3 g of the intermediate compound, maleic acid mono-α-tocopherol ester, obtained in Example 1 was dissolved in 30 ml of chloroform and reacted as in Example 1 with 1.3 g of γ-aminobutyric acid and 0.6 g of potassium hydroxide dissolved in 50 ml of N,N'-dimethylformamide according to the mixed anhydride method using 1.2 g of triethylamine and 1.3 g of ethyl chloroformate, and worked up as in Example 3 to give 4.0 g of sodium salt of the aimed compound, m.p. 203–205° C. (decomp.). Its IR spectrum is shown in FIG. 4. TLC: silica gel Rf=0.37 (n-butanol:acetic acid:water=4:1:1).

Elemental analyses: for $C_{47}H_{74}N_4O_{12}SNa_2 \cdot 1.5 H_2O$; Calculated (%): C, 56.90; H, 7.82; N, 5.65; Found (%): C, 57.18; H, 8.08; N, 5.77.

EXAMPLE 5

Figure 5:
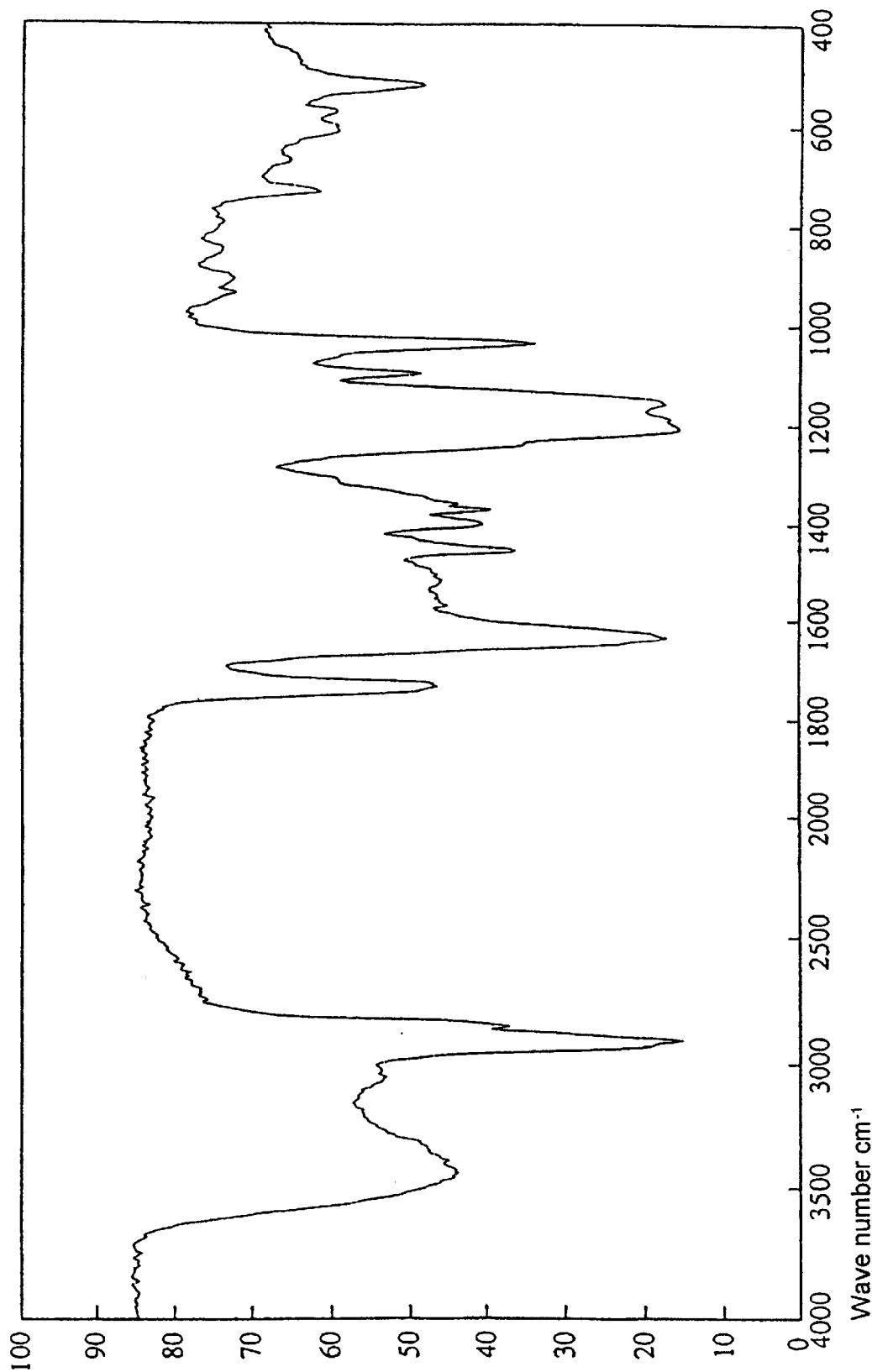
FIG. 5 shows an infrared spectrum (IR) of the compound synthesized in Example 5.

S-[2-(N-Carbonylaminoethylsulfonic acid)-1-(α-tocopheryl-6-yl-oxycarbonyl)ethyl]cysteine 2.4 g of 2-(N-carbonylaminoethylsulfonic acid)-1-(α-tocopheryl-6-yl-oxycarbonyl)ethylene sodium salt obtained in Example 2 was dissolved in 50 ml of methanol. To this was added 0.6 g of L-cysteine, and stirred for 2 hour at 50° C. After cooling, white crystals precipitated were collected by filtration, recrystallized from water/methanol to give 1.8 g of sodium salt of the aimed compound as white crystals, m.p. 200–202° C. (decomp.). Its IR spectrum is shown in FIG. 5. TLC: silica gel Rf=0.44 (n-butanol:acetic acid:water=4:1:1).

Elemental analyses: for $C_{38}H_{63}N_2O_9S_2Na.1.5\ H_2O$; Calculated (%): C, 56.62; H, 8.25; N, 3.48; Found (%): C, 56.65; H, 8.21, N, 3.42.

EXAMPLE 6

S-[2-(N-Carbonyl-3-β-aminoethyl-5-hydroxyindol)-1-(α-tocopheryl-6-yloxycarbonyl)ethyl]glutathione To 5.3 g of the intermediate compound, maleic acid mono-α-tocopherol ester, obtained in Example 1 and 1.2 g of triethylamine and 1.3 g of ethyl chloroformate was added 2.4 g of serotonin hydrochloride plus 1.5 g of triethylamine dissolved in 40 ml of methanol as in Example 1 according to the mixed anhydride method, and reacted as in Example 2. After evaporation of the solvent, the residual oil was extracted with ethyl acetate, washed with 1% acetic acid and then with water, and ethyl acetate was evaporated. After addition of ethanol, the mixture was let stand. White crystals precipitated, 2(N-carbonyl-3-ethylamino-5-hydroxyindol)-1-(α-tocopheryl-6-yl-oxycarbonyl)ethylene, were recrystallized from methanol to give 4.5 g of the product (m.p. 118–120° C.). To this product and 3.4 g of glutathione and 0.4 g of sodium hydroxide was added 70 ml of methanol, stirred for 3 hours at 50° C. The reaction mixture was concentrated to 30 ml, precipitated crystals collected and worked up as in Example 3 to give 3.7 g of sodium salt of the aimed compound, m.p. 202–204° C. (decomp.). TLC: silica gel Rf=0.46 (n-butanol:acetic acid:water=4:1:1).

Elemental analyses: for $C_{53}H_{78}N_5O_{11}SNa.2\ H_2O$; Calculated (%): C, 60.49; H, 7.85; N, 6.66; Found (%): C, 60.44; H, 7.81; N, 6.57.

EXAMPLE 7

S-[2-(N-Carbonyl-6-amino-n-caproic acid)-1-(α-tocopheryo-6-yl-oxycarbonyl)ethyl]glutathione Reaction was carried out using 5.3 g of the intermediate compound, maleic acid mono-α-tocopherol ester, obtained in Example 1, 1.2 g of triethylamine, 1.3 g of ethyl chloroformate and 1.5 g of ε-amino-n-caproic acid according to the mixed anhydride method and followed by workup as in Example 2. After evaporation of the solvent, water was added to the residue and the mixture was acidified with hydrochloric acid, and extracted with ethyl acetate. The extract was washed with water and then evaporated. The residue was dissolved in 70 ml of methanol and 3.3 g of glutathione was added to the solution. After adjusting its pH to 6.5 with sodium hydroxide/methanol, the mixture was stirred for 3 hours at 50° C. After cooling, precipitated crystals were collected by filtration and added to 50 m of water. The mixture was acidified with acetic acid, and crystals were collected, washed with water and then dissolved in THF/ ethanol. THF then was evaporated and the pH adjusted to 7 with sodium hydroxide/methanol. White crystals precipitated were collected by filtration and recrystallized from methanol/ethanol to give 2.5 g of disodium salt of the aimed compound, m.p. 199–201° C. (decomp.). TLC: silica gel Rf=0.38 (n-butanol:acetic acid:water=4:1:1).

Elemental analyses: for $C_{49}H_{78}N_4O_{12}SNa_2.2\ H_2O$; Calculated (%): C, 57.13; H, 8.02; N, 5.44; Found (%): C, 57.26; H, 8.09; N, 5.58.

EXAMPLE 8

S-[²-(N-Carbonyl-trans-4-aminomethylcyclohexanecarboxylic acid)-1-(α-tocopheryl-6-yl-oxycarbonyl)ethyl]glutathione Reaction and workup were carried out as in Example 7 using 5.3 g of the intermediate compound, maleic acid mono-α-tocopherol ester, obtained in Example 1, 1.2 g of triethylamine, 1.3 g of ethyl chloroformate and 1.7 g of tranexamic acid (trans-4-aminomethylcyclohexanecarboxylic acid) to give 2.2 g of disodium salt of the aimed compound, m.p. 210–212° C. (decomp.). TLC: silica gel Rf=0.45 (n-butanol:acetic acid:water=4:1:1).

Elemental analyses: for $C_{51}H_{80}N_4O_{12}SNa_2.3\ H_2O$; Calculated (%): C, 57.07; H, 8.07; N, 5.22; Found (%): C, 56.85; H, 8.08; N, 5.33.

EXAMPLE 9

S-[2-(N-Carbonylaminoethylsulfonic acid)-1-(α-tocopheryl-6-yl-oxycarbonyl)ethyl]γ-glutamylcysteine 50 ml of methanol was added to 2.6 g of 2-(N-carbonylaminoethylsulfonic acid)-1-(α-tocopheryl-6-yl-oxycarbonyl)ethylene sodium salt obtained in Example 2 and 1.0 g of γ-glutamylcysteine. The mixture was adjusted to pH6.5 with sodium hydroxide/methanol and stirred for 3 hours at 50° C. The reaction mixture then was concentrated to 20 ml and white crystals precipitated were collected by filtration and dissolved in 70 ml of water, acidified to pH 3 with hydrochloric acid. White crystals precipitated were collected by filtration. The crystals then were dissolved in THF/ethanol and the solution adjusted to pH 6.5 with sodium hydroxide/methanol. After evaporation of THF, precipitated crystals were collected by filtration, washed with a small amount of methanol, and recrystallized from methanol/ethanol to give 1.3 g of disodium salt of the aimed compound, m.p. 213–215° C. (decomp.). TLC: silica gel Rf=0.22 (n-butanol:acetic acid:water=4:1:1).

Elemental analyses: for $C_{43}H_{69}N_3O_{12}S_2Na_2.5\ H_2O$; Calculated (%): C, 50.62; H. 7.80; N, 4.12; Found (%): C, 50.42; H, 7.44; N, 4.48.

EXAMPLE 10

S-[2-(N-Carbonylaminoethylsulfonic acid)-1-(α-tocopheryl-6-yl-oxycarbonyl)ethyl]penicillamine Reaction and workup were carried out as in Example 5 using 3.2 g of 2-(N-carbonyl-aminoethylsulfonic acid)-1-(α-tocopheryl-6-yl-oxycarbonyl)ethylene sodium salt obtained in Example 2 and 0.8 g of D-penicillamine. Recrystallization from methanol/ethanol of the crystals thus obtained gave 2.5 g of sodium salt of the aimed compound, m.p. (starting gradual decomp. at about 190° C.). TLC: silica gel Rf=0.41 (n-butanol:acetic acid:water=4:1:1).

Elemental analyses: for $C_{40}H_{67}N_2O_9S_2Na.2.5\ H_2O$; Calculated (%): C, 56.38; H, 8.51; N, 3.29; Found (%): C, 56.12; H, 8.25; N, 3.57.

EXAMPLE 11

Figure 6:
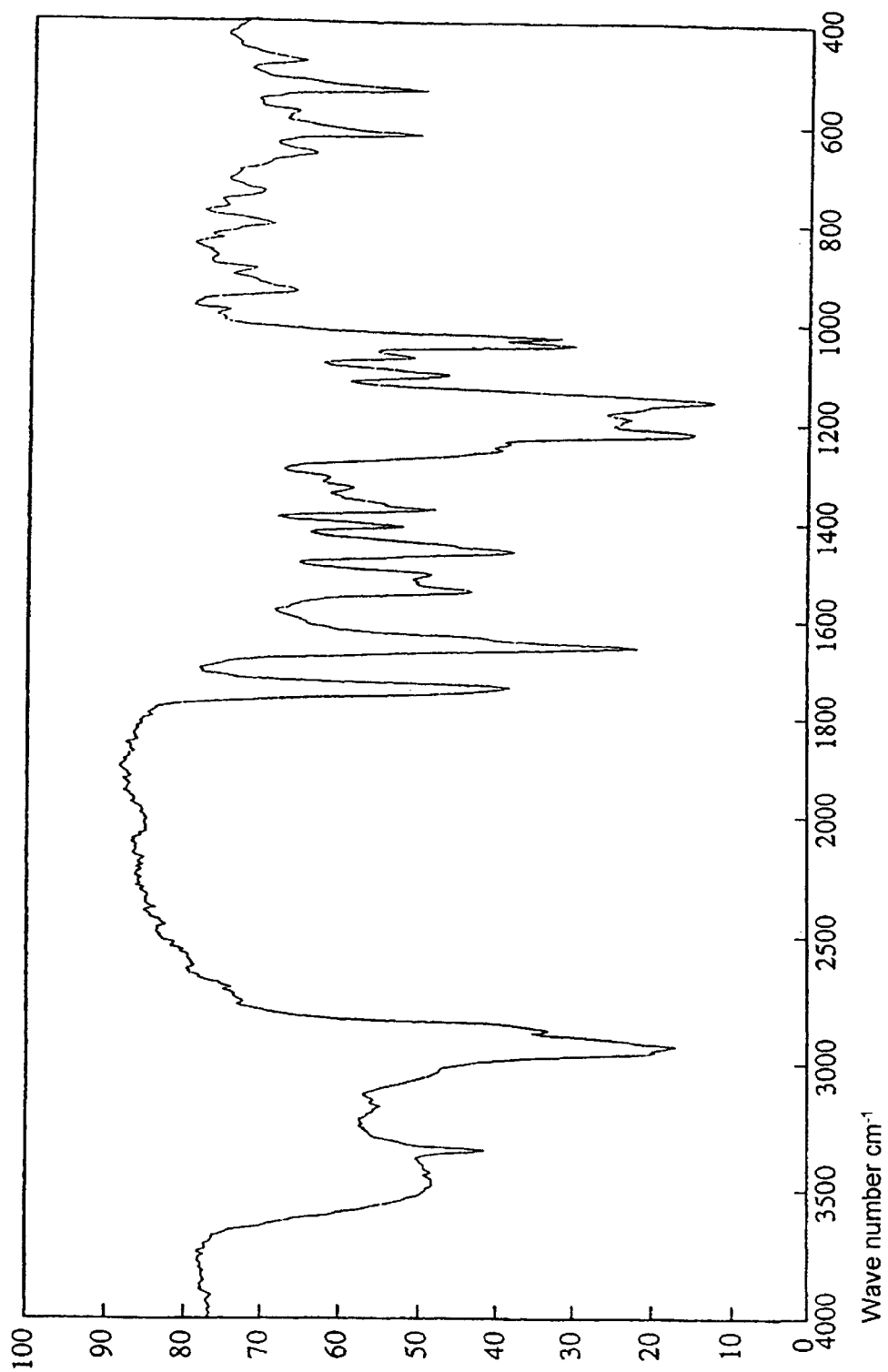
FIG. 6 shows an infrared spectrum (IR) of the compound synthesized in Example 11.

S-[2-(N-Carbonylaminoethylsulfonic acid)-1-(α-tocopheryl-6-yl-oxycarbonyl)ethyl]cysteamine 2.4 g of 2-(N-carbonylaminoethylsulfonic acid)-1-(α-tocopheryl-6-yl-oxy-carbonyl)ethylene sodium salt obtained in Example 2 and 0.5 g of cysteamine were dissolved in 70 ml of methanol. The solution was adjusted to pH 6 by addition of acetic acid and stirred for 3 hours at 50° C. After cooling, precipitated crystals were collected by filtration and suspended in methanol. The crystals were dissolved by adjusting the pH of the mixture to 6 by addition of sodium hydroxide/methanol, and then acidified with acetic acid. White crystals precipitated were collected by filtration, washed with methanol, and dried to give 1.3 g of the aimed compound as white crystals, m.p. 231–233° C. (decomp.). TLC: silica gel Rf=0.50 (n-butanol:acetic acid:water=4:1:1). Its IR spectrum is shown in FIG. 6.

Elemental analyses: for $C_{37}H_{64}N_2O_7S_2$; Calculated (%): C, 62.32; H, 9.05; N, 3.93;

Found (%): C, 62.41; H, 9.21; N, 3.81.

EXAMPLE 12

S-[2-(N-Carbonylglycineethyl)-1-(α-tocopheryl-6-yl-oxycarbonyl)ethyl]glutathione Reaction and workup were carried out as in Example 2 using 5.3 g of the intermediate compound, maleic acid mono-α-tocopherol ester, obtained in Example 1, 1.2 g of triethylamine, 1.3 g of ethyl chloroformate and 1.5 g of glycineethyl hydrochloride according to the mixed anhydride method. After evaporation of the solvent, extraction with ethyl acetate and washing with 3% sodium bicarbonate, 1 N hydrochloric acid and then with water in this order, followed by evaporation of ethyl acetate, gave about 6 g of residual oil. This was dissolved in 50 ml of methanol. Separately, 3.3 g of glutathione and 0.5 g of sodium hydroxide were dissolved in 50 ml of 70% methanol. This solution was added to the above methanol solution and the mixture was stirred for 2 hours at 50° C. After evaporation of the solvent, crystals precipitated by addition of ethanol were collected by filtration and dissolved in 50 ml of water. To the solution was added hydrochloric acid, and white crystals precipitated were collected by filtration, dissolved in THF/ethanol (1:1) and worked up as in Example 7 to give 2.0 g of sodium salt of the aimed compound, m.p. 195–197° C. (decomp.). TLC: silica gel Rf=0.40 (n-butanol:acetic acid:water=4:1:1).

Elemental analyses: for $C_{47}H_{75}N_4O_{12}SNa.2.5\ H_2O$; Calculated (%): C, 57.12; H 8.16; N, 5.67; Found (%): C, 57.22; H, 7.94 N, 5.92.

EXAMPLE 13

S-[2-(N-Carbonylaminoethylsulfonic acid)-1-(α-tocopheryl-6-yl-oxycarbonyl)ethyl]glutathione Isopropyl Ester To 4.0 g glutathione isopropyl ester sulfuric acid salt (γ-glutamylcysteinylglycine isopropyl ester sulfuric acid salt) suspended in 60 ml of water was gradually added 2 N sodium hydroxide to raise the pH to 4 to make a solution, and the solution was concentrated. To this was added 100 ml of 80% methanol and 4.8 g of 2-(N-carbonylaminoethylsulfonic acid)-1-(α-tocopheryl-6-yl-oxycarbonyl)ethylene sodium salt obtained in Example 2, and the mixture was stirred for 3 hours at 50° C. After evaporation of about 60 ml of the solvent, precipitated crystals were collected by filtration, dissolved in THF-methanol (1:1) and insoluble matters were filtered out. After evaporation of the solvent, ethanol was added to the crystalline residue and the crystals were collected by filtration. Recrystallization from methanol/ethanol of the crystals gave 3.6 g of sodium salt of the aimed compound as white crystals, m.p. (stating decomp. at about 205° C.). TLC: silica gel Rf=0.39 (n-butanol:acetic acid:water=4:1:1).

Elemental analyses: for $C_{48}H_{79}N_4O_{13}S_2Na.2\ H_2O$; Calculated (%): C, 55.26; H, 8.02; N, 5.37; Found (%): C, 55.08; H, 8.01; N, 5.37.

EXAMPLE 14

S-[2-(N-Carbonylaminoethylsulfinic acid)-1-(α-tocopheryl-6-yl-oxycarbonyl)ethyl]glutathione Using 1.5 g of hypotaurine in place of ε-amino-n-caproic acid used in Example 7, reaction and workup were carried out as in Example 2 to give 3.9 g of sodium salt of the aimed compound, m.p. (starting gradual decomp. at about 203° C.). TLC: silica gel Rf=0.38 (n-butanol:acetic acid:water=4:1:1).

Elemental analyses: for $C_{45}H_{73}N_4O_{12}S_2Na.\ H_2O$; Calculated (%): C, 55.88; H, 7.82; N, 5.79; Found (%): C, 55.69; H, 7.80; N, 5.58.

Example 15

S-[2-(N-Carboxypropyl)-1-(α-tocopheryl-6-yl-oxycarbonyl)ethyl]-glutathione

Using 1.5 g of L-proline in place of ε-amino-n-caproic acid used in Example 7, reaction and workup were carried out as in Example 2 to give 3.9 g of sodium salt of the aimed compound, m.p. (starting gradual decomp. at about 215° C.). TLC: silica gel Rf=0.30 (n-butanol:acetic acid:water=4:1:1).

Elemental analyses: for $C_{48}H_{74}N_4O_{12}SNa_2.H_2O$; Calculated (%): C, 58.05; H, 7.71; N, 5.64; Found (%): C, 57.97; H, 7.91; N, 5.39.

EXAMPLE 16

Effect of the Present Compound on Acetaminophen-induced Hepatopathy in Mice

The present compound was examined for the effect on acetaminophen-induced hepatopathy in mice.

Test Compound:

The compound of Example 2 (abbreviated to ETS-GS-Na) 0.1 mmol/ 10 ml/kg, i.p.

Test Method:

7-week old male ddy mice purchased from SLC Japan (Kabushiki Kaisha) were used for the test following a 24-hour fasting.

Hepatopathy was induced by oral administration of 250 mg/10 ml/kg acetaminophen (dissolved by warming).

24 hours after the oral administration of acetaminophen, blood were sampled for measurement of GOP and GPT activities, indices of hepatopathy. The mice were kept on fasting for 48 hours until the blood sampling was made.

The test compound was intraperitoneally injected 30 min before the administration of acetaminophen.

Figure 7A:
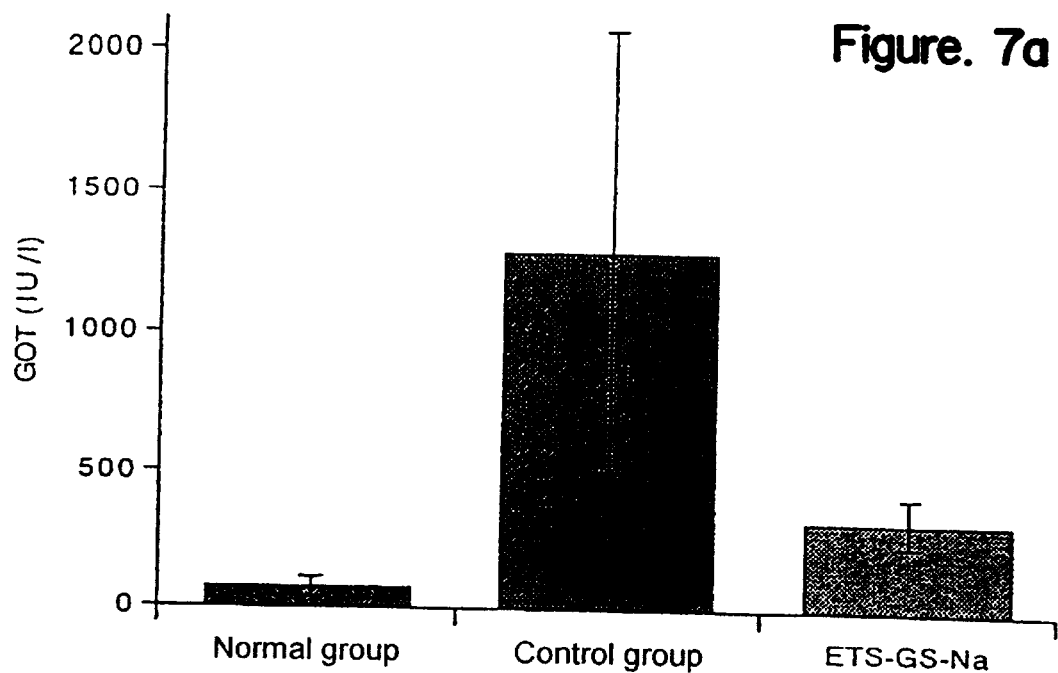
FIG. 7a is a graph illustrating the effect of the present compound against rat BSO cataract.
Figure 7B:
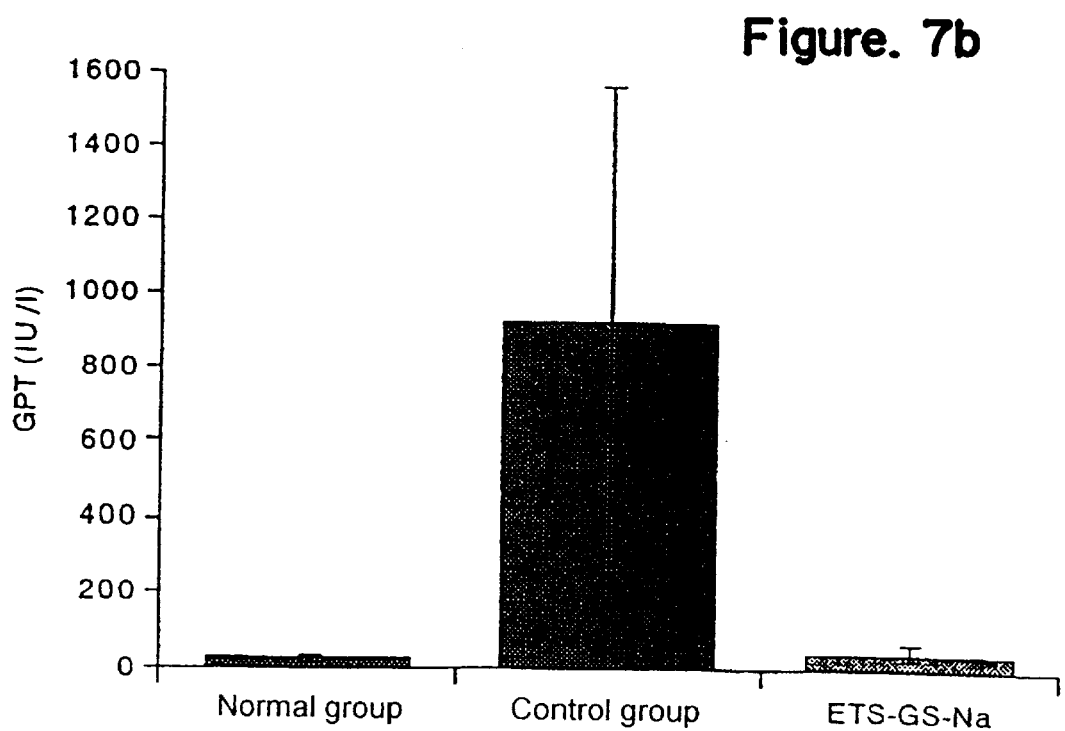
FIG. 7b is a graph illustrating the effect of the present compound against rat BSO cataract.
Figure 8:
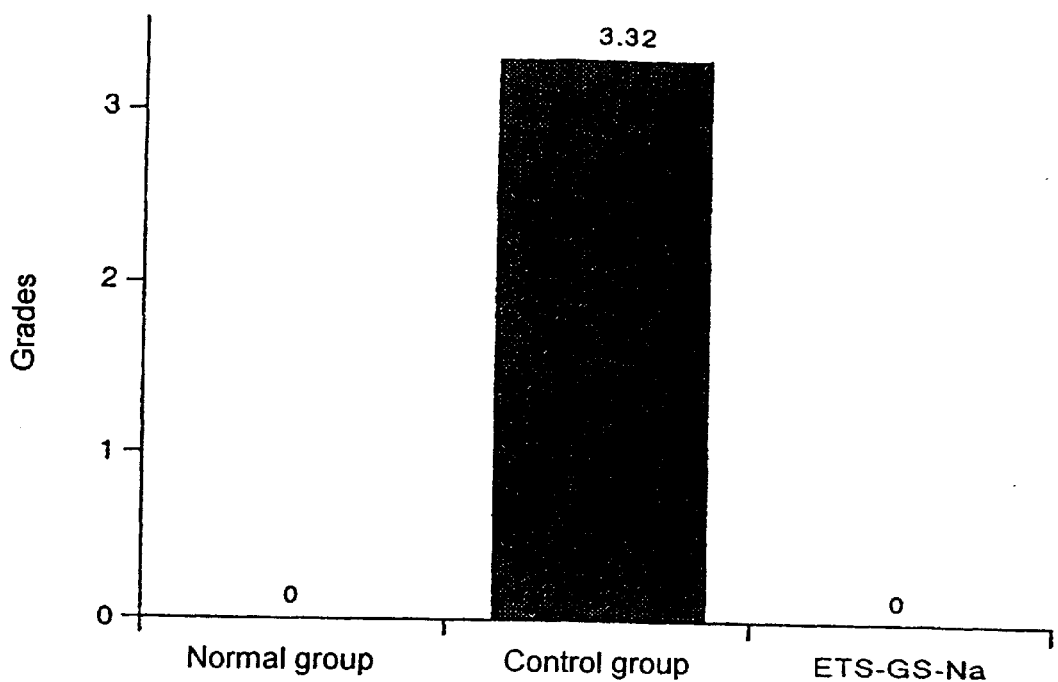
FIG. 8 is a graph illustrating the effect of the present compound against rat BSO cataract.

Test Results:

Oral administration of acetaminophen to the mice increased blood GOT and GPT activities to 1294±788 and 926±649 IU/1 (73.9±36.47 and 25.44±12.31 IU/1, respectively, for normal groups), respectively, 24 hours after the administration. In contrast, the values were 336±89 and 47±22, respectively, for the group to which the present compound was administered, demonstrating a significant suppressing effect on acetaminophen-induced hepatopathy. FIGS. 7a and 7b show a graphic expression of these values.

The results revealed that the present compound is useful as a hepatopathy suppressing agent.

EXAMPLE 17

Effect of the Present Compound on BSO-induced Cataract in Rats

The present compound was examined for the effect on buthionine sulfoximine (BSO)-induced cataract in rats.

Test Compound:

The compound of Example 2 (abbreviated to ETS-GS-Na) 0.1 mmol/10 ml/kg, i.p.

Test Method:

The test was performed according to the method of Maitra et al.

Indrani Maitra, Elena Serbinova et al., α-Lipoic Acid Prevents Buthionine Sulfoximine-induced Cataract Formation in Newborn Rats Free Radical Biology & Medicine, Vol. 18, No. 4, pp.823–829, 1995.

28 to 36-hour old SD rats purchased from SLC Japan (Kabushiki Kaisha) were used for the test.

Cataract was induced by subcutaneously administering 3 mmol/kg of BSO at 8:00 A.M. and 4:00 P.M. for 2 days. Observation of cataract was performed using a slit lamp microscope after the newborn rats opened their eyes after the BSO administration. The opacity of each of the lenses was assessed and classified into one of the following 0–5 grades.

0: a clear lens without opacity

1: a lens with opacities in part of the equatorial region

2: a lens with opacities along the equatorial region

3: a lens with opacities in part of the cortex

4: a lens with opacities in the whole cortex

5: a lens with opacities advancing up to the central region.

The test compound was intraperitoneally administered 4 and 12 hours after the administration of BSO.

Test Results:

As a result of the subcutaneous injection of 3 mmol/kg of BSO into the SD rats, opacities of the lenses were observed, with their average grade in 3.32. In contrast, no opacities were observed, i.e., the average grade being 0, for the group treated with the test compound, demonstrating a complete suppression of BSO-induced cataract.

The results revealed that the present compound is useful as an anticataract agent.

EXAMPLE 18

Effect of the Present Compound on the Formation of Lipid Peroxide Through the Autoxidation of Rat Brain Homogenate The present compound was examined for the effect on the formation of lipid peroxide through the autoxidation of a rat brain homogenate.

Test Compound:

The compound of Example 1 (abbreviated to ES-GS-Na)

The compound of Example 5 (abbreviated to ETS-Cys-Na)

Test Method:

1) Preparation of a Brain Homogenate and Formation of Lipid Peroxide Through Autoxidation Wistars rat (purchased from SLC Japan (Kabushiki Kaisha)) were decapitated without anesthesia and the skull was immediately opened and the brain removed. The brain taken out was washed with ice-cooled, phoshate buffered saline (PBS (50 mM, pH 7.4)), lightly blotted with filter paper and weighed. Four times ice-cooled PBS was added to the brain and homogenized in ice. The homogenate was centrifuged at 1000×g (2700 rpm) for 10 min at 0° C. The supernate thus obtained was used for the test. To 100 μl of the test compound were added 700 μl of PBS and 200 μl of the supernate of the brain homogenate, and incubated at 37° C. for 30 min. A control group and a blank group were incubated with PBS, with the blank group at 0° C. for 30 min. Then, 200 μl of 35% perchloric acid was added to cease the reaction and the mixture was centrifuged at 1300×g (3200 rpm) for 10 min at 0° C. Using the supernate as a sample, the amount of malondialdehyde (MDA) formed was determined by thiobarbituric acid colorimetric method (TBA method).

2) Preparation of Standards

To 0.11 g (0.5 mmol) of 1,1,3,3-tetraethoxypropane was added methanol to make 50 ml of volume. This solution was diluted $10^3$, $3\times10^3$ and $10^4$-folds with methanol and used as the standards (10 μM, 3 μM, 1 μM). Methanol was assigned to 0 μM.

3) Determination of MDA Formed by TBA Method

To 1 ml of each of the samples or the standards were added 0.2 ml of 8.1% sodium dodecylsulfate (SDS), 1.5 ml of 20% acetate buffer (pH 3.5) and 0.8% thbiobarbituric acid (TBA) and incubated in a boiling water bath for 60 min. After ice-cooling to cease the reaction, 4 ml of butanol-pyridine (15:1) was added and mixed well. After centrifugation at 1200×g (3000 rpm) for 10 min, the fluorescence intensity of the butanol-pyridine layer was measured at the wavelength of 553 nm with the excitation wavelength of 515 nm.

4) Calculation of the Rate of Suppression of Lipid Peroxide Formation

The rate of suppression of lipid peroxide formation was calculated according to the following equation for each test compound.

Rate of suppression of lipid peroxide formation (%)=[1-(C-A/B-A)]×100

A: Amount (μM) of formed MDA for the blank group

B: Amount (μM) of formed MDA for the control group

C: Amount (μM) of formed MDA for a test compound group

Test Results:

The result is shown in Table 1.

TABLE 1

Effect of the present compound on the formulation of lipid peroxide through the autoxidation of rat brain homogenate

| | | Amount of MDA (μM) | Rate of Suppression (%) |
|---|---|---|---|
| Blank | | 0.473 ± 0.026 | — |
| Control Group | | 6.500 ± 0.375 | — |
| Compound of Example 1 | $3 \times 10^{-5}$M | 0.838 ± 0.056 | 93.94 *3 |
| | $10^{-5}$M | 1.338 ± 0.039 | 85.64 *3 |
| | $3 \times 10^{-6}$M | 4.079 ± 0.126 | 40.17 *3 |
| | $10^{-6}$M | 5.208 ± 0.083 | 21.43 *2 |
| Compound of Example 5 | $3 \times 10^{-5}$M | 0.980 ± 0.249 | 91.59 *3 |
| | $10^{-5}$M | 4.090 ± 0.348 | 39.98 *2 |
| | $3 \times 10^{-6}$M | 4.890 ± 0.052 | 26.71 *2 |
| | $10^{-6}$M | 5.022 ± 0.060 | 24.52 *2 |

The values indicate mean ± standard deviation (n = 3).
Significance from the control group *1; $p < 0.05$, *2; $p < 0.01$, *3; $p < 0.001$ As evident from Table 1, the present compound, at $10^{-6}$ to $3\times10^{-5}$ M, significantly and dose-dependently suppressed formation of lipid peroxide through autoxidation of rat brain homogenate.

The results revealed that the present compound has an antioxidant activity and useful as a cerebral metabolism improving agent.

[Composition Example 1]

Oral tablets

| | |
|---|---|
| Compound of Example 2 | 30 mg |
| Lactose | 80 mg |
| Potato starch | 17 mg |
| Polyethylene glycol 6000 | 3 mg |

Tablets are made by a conventional method based on the above components for one tablet.

[Composition Example 2]

Eye drops

| | |
|---|---|
| Compound of Example 2 | 0.3 g |
| Glycerol | 2.5 g |
| Methyl p-hydroxybenzoate | 0.026 g |
| Propyl p-hydroxybenzoate | 0.014 g |
| Sodium acetate | q.s. |
| Sterile purified water | to 100 ml pH 6.5 |

The above components are mixed and sterilized by filtration to give eye drops.

[Composition Example 3]

Injection

| | |
|---|---|
| Compound of Example 4 | 0.5 g |
| Mannitol | 5.0 g |
| Distilled water for injection | to 100 ml pH 6.5 |

[Composition Example 4]

Cosmetic cream

| | |
|---|---|
| Compound of Example 3 | 0.3 g |
| Stearic acid | 2.0 g |
| Stearyl alcohol | 7.0 g |
| Squalane | 5.0 g |
| Octyldecanol | 6.0 g |
| Polyoxyethylene (15) cetyl ether | 3.0 g |
| Glyceryl monostearate | 2.0 g |
| Propylene glycol | 5.0 g |
| Methyl p-hydroxybenzoate | 0.2 g |
| Propyl p-hydroxybenzoate | 0.1 g |
| Sterile purified water | 68.7 g |

The above components are mixed to form a cosmetic cream.

INDUSTRIAL APPLICABILITY

As provided as non-hygroscopic, stable crystals soluble in water, and thus allowing easy incorporation into composition forms, the vitamin E derivatives of the present invention are advantageously used as hepatopathy suppressing agents, anticataract agents, cerebral metabolism improving agents, and antioxidants, as well as cosmetic components.

What is claimed is:

1. A vitamin E derivative represented by the following formula (I) wherein: $R_1$ and $R_2$ are the same or different and each denotes hydrogen or methyl, $R_3$ denotes one of the S-linked SH compounds as defined hereinbelow or an ester thereof (except esters of cyteamine), and $R_4$ denotes hydroxyl, one of the compounds (6)–(11) as defined hereinbelow or an ester of one of the compounds (6)–(9) or the compound (12) as defined hereinbelow, or a pharmacologically acceptable salt thereof.

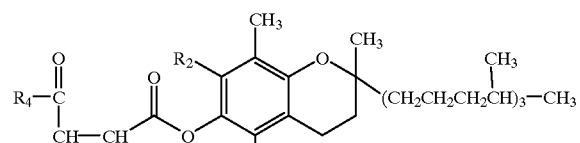

(I)

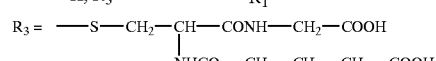

$R_3 =$ 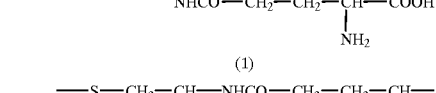

(1)

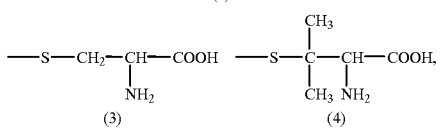

(2)

(3)         (4)

(5)

$R_4 =$ —NH(CH$_2$)$_n$COOH (n = 1–5),
(6)

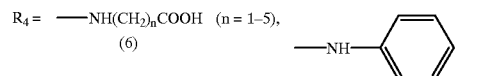

(7)

(8)         (9)

—NHCH$_2$CH$_2$SO$_3$H,   —NHCH$_2$CH$_2$SO$_2$H
(10)                      (11)

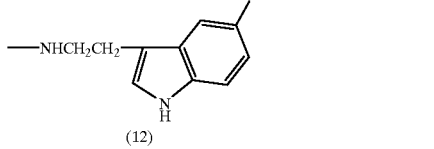

(12)

2. The vitamin E derivative of claim 1 which is S-[2-carboxy-1-(α-tocopheryl-6-yl-oxycarbonyl)ethyl] glutathione or a pharmacologically acceptable salt thereof.

3. The vitamin E derivative of claim 1 which is S-[2-(N-carbonylaminoethylsulfonic acid)-1-(α-tocopheryl-6-yl-oxycarbonyl)ethyl]glutathione or a pharmacologically acceptable salt thereof.

4. The vitamin E derivative of claim 1 which is S-[2-(N-carbonylanthranilic acid)-1-(α-tocopheryl-6-yl-oxycarbonyl)ethyl]glutathione or a pharmacologically acceptable thereof.

5. The vitamin E derivative of claim 1 which is S-[2-(N-carbonyl-γ-aminobutyric acid)-1-(α-tocopheryl-6-yl-oxycarbonyl)ethyl]glutathione or a pharmacologically acceptable salt thereof.

6. The vitamin E derivative of claim 1 which is S-[2-(N-carbonylaminoethylsulfonic acid)-1-(α-tocopheryl-6-yl-oxycarbonyl)ethyl]cysteine or a pharmacologically acceptable salt thereof.

7. The vitamin E derivative of claim 1 which is S-[2-(N-carbonyl-3-β-aminoethyl-5 hydroxyindol)-1-(α-tocopheryl-6-yl-oxycarbonyl)ethyl]glutathione or a pharmacologically acceptable salt thereof.

8. The vitamin E derivative of claim 1 which is S-[2-(N-carbonyl- 6-amino-n-caproic acid)-1-(α-tocopheryl-6-yl-oxycarbonyl)ethyl]glutathione or a pharmacologically acceptable salt thereof.

9. The vitamin E derivative of claim 1 which is S-[2-(N-carbonyl-trans-4-aminomethylcyclohexanecarboxylic acid)-1-(α-tocopheryl-6-yl-oxycarbonyl)ethyl]glutathione or a pharmacologically acceptable salt thereof.

10. The vitamin E derivative of claim 1 which is S-[2-(N-carbonylaminoethylsulfonic acid)-1-(α-tocopheryl-6-yl-oxycarbonyl)ethyl]γ-glutamylcysteine or a pharmacologically acceptable salt thereof.

11. The vitamin E derivative of claim 1 which is S-[2-(N-carbonylaminoethylsulfonic acid)-1-(α-tocopheryl-6-yl-oxycarbonyl)ethyl]penicillamine or a pharmacologically acceptable salt thereof.

12. The vitamin E derivative of claim 1 which is S-[2-(N-carbonylaminoethylsulfonic acid)-1(α-tocopheryl-6-yl-oxycarbonyl)ethyl]cysteamine or a pharmacologically acceptable salt thereof.

13. The vitamin E derivative of claim 1 which is S-[2-(N-carbonylglycineethyl)-1-(α-tocopheryl-6-yl-oxycarbonyl)ethyl]glutathione or a pharmacologically acceptable salt thereof.

14. The vitamin E derivative of claim 1 which is S-[2-(N-carbonylaminoethylsulfonic acid)-1-(α-tocopheryl-6-yl-oxycarbonyl)ethyl]gluta-thione isopropyl ester or a pharmacologically acceptable salt thereof.

15. The vitamin E derivative of claim 1 which is S-[2-(N-carbonylaminoethylsulfinic acid)-1-(α-tocopheryl-6-yl-oxycarbonyl)ethyl]glutathione or a pharmacologically acceptable salt thereof.

16. The vitamin E derivative of claim 1 which is S-[2-(N-carboxypropyl)-1-(α-tocopheryl-6-yl-oxycarbonyl)ethyl]glutathione or a pharmacologically acceptable salt thereof.

17. A method for preparation of the vitamin E derivative of claim 1 or a pharmacologically acceptable salt thereof which comprises: reacting vitamin E with maleic anhydride to produce mono-tocopheryl maleate (or fumarate) and then subjecting the thus produced mono-tocopheryl maleate (or fumarate) to an addition reaction with a compound selected from the group of SH compounds consisting of glutathione, γ-glutamylcysteine, cysteine, penicillamine, an ester thereof, and cysteamine.

18. A method for preparation of the vitamin E derivative of claim 1 or a pharmacologically acceptable salt thereof which comprises: reacting vitamin E with maleic anhydride to produce mono-tocopheryl maleate (or fumarate) and then subjecting the thus produced mono-tocopheryl maleate (or fumarate) to a condensation reaction with a compound selected from the group of amino acids consisting of glycine, β-alanine, γ-aminobutyric acid, 5-aminovaleric acid, ε-aminocaproic acid, anthranilic acid, tranexamic acid, proline, esters thereof, aminoethylsulfonic acid and aminoethylsulfinic acid or with serotonin by the mixed acid anhydride method to produce a corresponding acid amide of the mono-tocopheryl maleate (or fumarate), and then subjecting the product to an addition reaction with a compound selected from the group of SH compounds consisting of glutathione, γ-glutamylcysteine, cysteine, penicillamine, esters thereof, and cysteamine.

19. A hepatopathy suppressing pharmaceutical composition comprising the vitamin E derivative of claim 1 or a pharmacologically acceptable salt thereof.

20. An anticataract pharmaceutical composition comprising the vitamin E derivative of claim 1 or a pharmacologically acceptable salt thereof.

21. A cerebral metabolism improving pharmaceutical composition comprising the vitamin E derivative of claim 1 or a pharmacologically acceptable salt thereof.

22. An antioxidant pharmaceutical composition comprising the vitamin E derivative of claim 1 or a pharmacologically acceptable salt thereof.

23. A cosmetic composition comprising the vitamin E derivative of claim 1 or pharmacologically acceptable salt thereof.

* * * * *